United States Patent [19]
Denker

[11] Patent Number: 6,123,724
[45] Date of Patent: Sep. 26, 2000

[54] HEART ASSIST METHOD AND APPARATUS EMPLOYING MAGNETIC REPULSION FORCE

[76] Inventor: Stephen Denker, 2130 W. Columbia Dr., Mequon, Wis. 53092

[21] Appl. No.: 09/291,567

[22] Filed: Apr. 14, 1999

[51] Int. Cl.[7] .................................................. A61M 1/12
[52] U.S. Cl. ............................................ 623/3.11; 600/17
[58] Field of Search ............................ 623/3, 3.11, 3.27, 623/3.28; 600/16, 17

[56] References Cited

U.S. PATENT DOCUMENTS

| | | | |
|---|---|---|---|
| 3,433,983 | 3/1969 | Keistman et al. | ...................... 600/16 X |
| 3,949,757 | 4/1976 | Sabel . | |
| 4,176,411 | 12/1979 | Runge . | |
| 4,454,883 | 6/1984 | Fellus . | |
| 4,621,617 | 11/1986 | Sharma | ...................................... 623/3 X |
| 4,809,713 | 3/1989 | Grayzel . | |
| 5,170,784 | 12/1992 | Ramon et al. . | |
| 5,300,111 | 4/1994 | Panton et al. | .................................. 623/3 |
| 5,498,228 | 3/1996 | Royalty et al. | ............................ 600/16 |
| 5,674,271 | 10/1997 | Denker . | |

FOREIGN PATENT DOCUMENTS

| | | | |
|---|---|---|---|
| 2 485 928 | 1/1982 | France | ......................................... 623/3 |
| 1 444 614 | 8/1976 | United Kingdom | ....................... 623/3 |

*Primary Examiner*—David H. Willse
*Attorney, Agent, or Firm*—Quarles & Brady LLP; George E. Haas

[57] ABSTRACT

A heart is artificially contracted to pump blood an artificial device that employs electromagnetic force. That device includes electromagnetic coils attached to ribs of the animal and permanent magnets are placed adjacent the electromagnetic coils. When direct electric currents are applied to the electromagnetic coils the magnetic fields from the coils and the permanent magnets interact to repel permanent magnets which apply contraction force to the heart.

17 Claims, 2 Drawing Sheets

HEART ASSIST METHOD AND APPARATUS EMPLOYING MAGNETIC REPULSION FORCE

BACKGROUND OF THE INVENTION

The present invention relates to artificial devices for assisting the pumping action of a heart.

Cardiac disorders often prevent the heart from being able to contract properly and pump blood through the arteries. One treatment involves surgically implanting an artificial pacing device with electrodes attached to the surface or inside of the heart. A controller of the implanted pacing device periodically sends electrical pulses to the electrodes which electrically stimulate the heart muscle to contract and pump blood from the heart chambers. This pacing action controls the contraction of the heart thereby providing a natural pumping action of the blood.

Individuals with more severe cardiac disease may not be eligible for conventional pacing as the muscles of the heart have deteriorated so significantly that external stimulation will not produce sufficient pumping action. Treatment of these individuals may involve cutting away a portion of a ventricle of the heart and implanting an artificial pump in the opening. The artificial pump supplements the heart's pumping action. This radical solution often is the last option available for the patient, as it permanently removes part of the heart where the artificial pump is inserted. Typically this treatment is used only to prolong a person's life long enough to find a donor heart for transplantation.

Therefore, it is desirable to provide a technique for artificially inducing contraction of a heart in individuals with significant muscle deterioration, where the procedure is less invasive and less radical than the surgical implantation of an artificial pump.

SUMMARY OF THE INVENTION

A general object of the present invention is to provide a technique and apparatus for artificially contracting chambers of the heart to pump blood in situations where conventional cardiac pacing may be insufficient. This invention enhances the cardiac output of the heart.

Another object of the present invention is to utilize electromagnetic fields to assist contraction of the heart chambers.

A further object is to employ repulsion forces developed between two or more magnets to assist cardiac function.

These and other objectives are satisfied by an apparatus for artificially contracting a heart of an animal to pump blood. That apparatus includes a first electromagnet coil adapted to be attached to a bone of the animal and which produces an electromagnetic field when an electric current is applied thereto. A first permanent magnet is disposed adjacent both the first electromagnet coil and the heart. The first permanent magnet produces a magnetic field which repulsively interacts with the electromagnetic field causing the first permanent magnet to apply a contracting force to the heart.

In one embodiment of the invention the permanent magnet is attached to the exterior surface of the heart. In another embodiment, the apparatus has the form of a solenoid in which the permanent magnet is attached to an armature that moves with respect to the electromagnetic coil. In the latter version, magnetic field interaction moves the armature away from the electromagnetic coil and pushes against the heart.

DETAILED DESCRIPTION OF THE INVENTION

Figure 1:
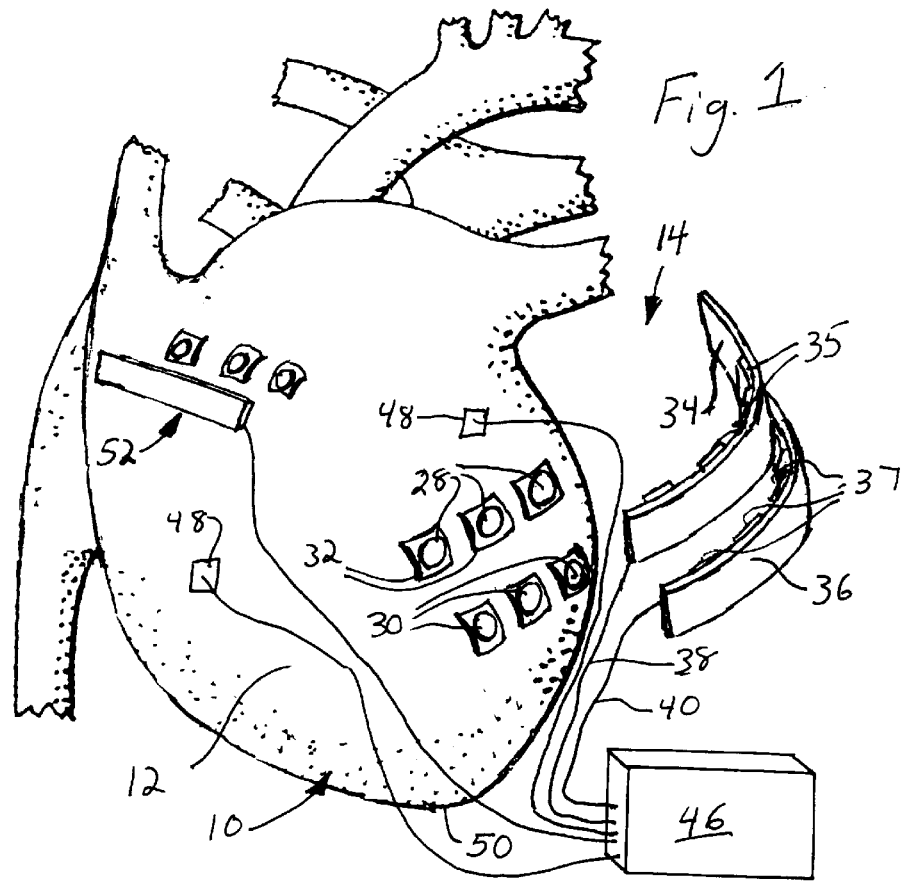
FIG. 1 is a conceptual view of a human heart to which the present technique is being applied.

With initial reference to FIG. 1, a human heart 10 has an exterior surface 12. For hearts which are unable to pump an adequate amount of blood to the body, an artificial contraction assist device 14 is implanted into the patient. Using known procedures, the chest of the patient is opened to insert the components of the device.

A plurality of permanent magnets 28 and 30, such as rare earth magnets, is applied to the exterior surface 12 of the heart 10 outside the left ventricle. The permanent magnets 28 and 30 are mounted on pads 32 which are attached to the heart by sutures, surgical adhesive or similar means. A first group of the permanent magnets 28 is placed on a first circumferential line around the heart and second group of permanent magnets 30 is placed on a second circumferential line. Preferably the second circumferential line is substantially parallel to the first circumferential line. For purposes of this disclosure, the term "magnet" means a member or material which already has been magnetized so as to produce a magnetic field or which produces a magnetic field upon application of electricity. In contrast, the term "magnetic" means a member or material which has a sufficient magnetic susceptibility so as to be capable of being repelled or attracted by a magnetic field.

Figure 2:
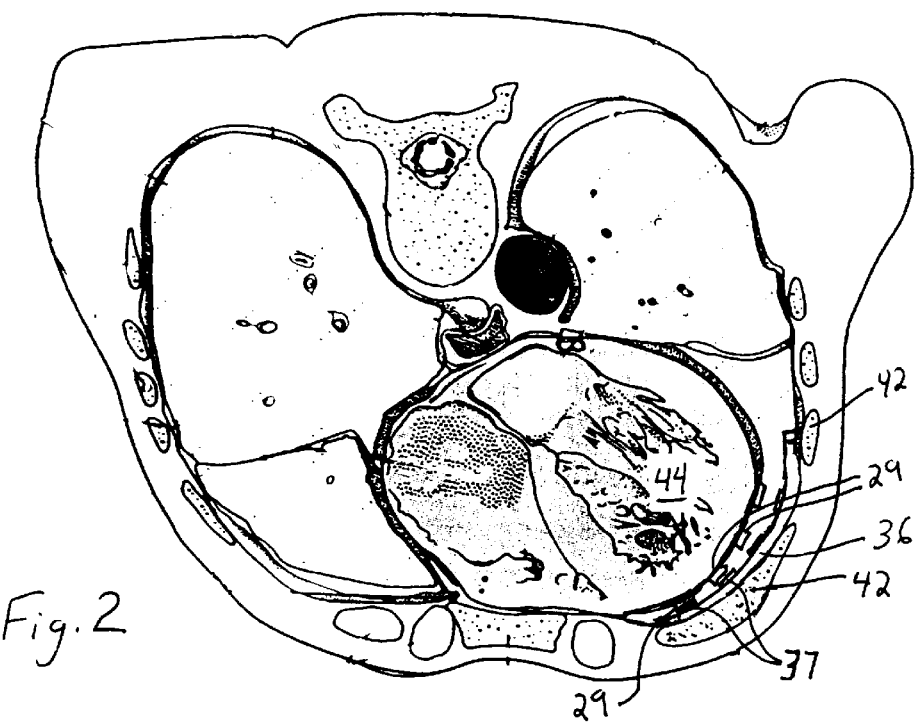
FIG. 2 is transverse cross sectional view through the upper thorax of a human in which the present cardiac assist apparatus has been implanted.

A pair of brackets 34 and 36 are secured to the ribs 42 of the patient by any one of several suitable mechanisms. Each bracket 34 and 36 is aligned with either the first or second groups of permanent magnets 28 and 30 and has a plurality of electromagnet coils 35 and 37 each lying adjacent to one of the permanent magnets 28 and 30, respectively. As shown in FIG. 2, the second bracket 36 is attached to ribs 42 so that its coils 37 are aligned with the permanent magnets 30 in the second group. It should be understood that a greater number of adjacent rows of permanent magnets and brackets with electromagnet coils may be used, as well as varying numbers of magnets and coils in each row.

Each electromagnet coil 35 and 37 has a shape conforming to the shape of a permanent magnet 28 or 30, and preferably comprises a flexible magnetically permeable substrate on which spiral shaped coil is mounted. The electromagnet coil can be formed by a wire that is wound in a spiral on the substrate surface or can be formed by a thin layer of electrically conductive material that has been etched to form the spiral pattern. Pairs of electrical wires 38 and 40 are connected to the ends of electromagnet coils 35 and 37, respectively.

Referring still to FIGS. 1 and 2, the wires from the electromagnetic coils 35 and 37 extend to a controller 46. The controller also received input signals from sensor electrodes 48 on the surface 12 of the heart 10 which indicate when the heart is contracting. This controller 46 is similar to prior cardiac pacing devices which produce electrical pulses applied to electrodes that stimulate a responsive contraction of the heart muscles. However, the present controller 46 applies pulses of electric current through the various coils 35 and 37 to generate magnetic fields that repel the permanent magnets 28 and 30 in a controlled manner, rather than to electrodes to electrically stimulate the heart.

The natural contraction of left ventricle 44 is detected by sensors 48 which signal the controller 46 to apply electrical pulses of direct current to the electromagnetic coils 35 and 37. The electric current flowing through those coils produce electromagnetic fields adjacent to the heart surface. Due to the direction of the direct current, the resultant magnetic fields are polarized so that the permanent magnets 28 and 30 are repelled from electromagnetic coils 35 and 37. That magnetic repulsion forces the heart wall inward causing a contraction of the left ventricle 44 in much the same manner as though the heart muscles contracted the ventricle. The duration of the electrical pulse is equal to that of the desired contraction.

The present apparatus 14 has particular application in assisting a patient who has some cardiac function, which is a fraction (e.g. 50%) of the normal function. In this situation, the electrical pulses are applied at the end of the natural heart contraction to compress the left ventricle 44 the remaining amount necessary to achieve a normal cardiac output. Thus the present technique increases the efficiency of a defective heart.

The controller 46 can be programmed so that the external electromagnetic coils 35 and 37 are pulsed separately or simultaneously. For example, the sets of electromagnet coils 35 and 37 may be pulsed sequentially to squeeze the left ventricle 44 in a progressive manner from the apex 50 upward to the base of the heart to pump the blood upward through the ventricle. In addition, the magnitude of electrical current applied to each coil can be regulated independently to produce the desired amount of heart contraction in corresponding regions of the heart 10.

The cardiac assist device 14 also may be used to assist the heart filling with blood. For that effect, the current through the electromagnetic coils 35 and 37 is reversed during diastole to produce magnetic attraction between the coils and the permanent magnets 28 and 30. That attraction pulls the exterior surface 12 of the heart outward enlarging the left ventricle 44 and drawing blood into the heart.

The pumping of the right ventrical also can be assisted by placing the present device 14 outside that portion of the heart. In addition, cardiac assist device 14 can be applied to one or both of the atria such as is shown at 52 in FIG. 1 for the right atrium.

Figure 3:
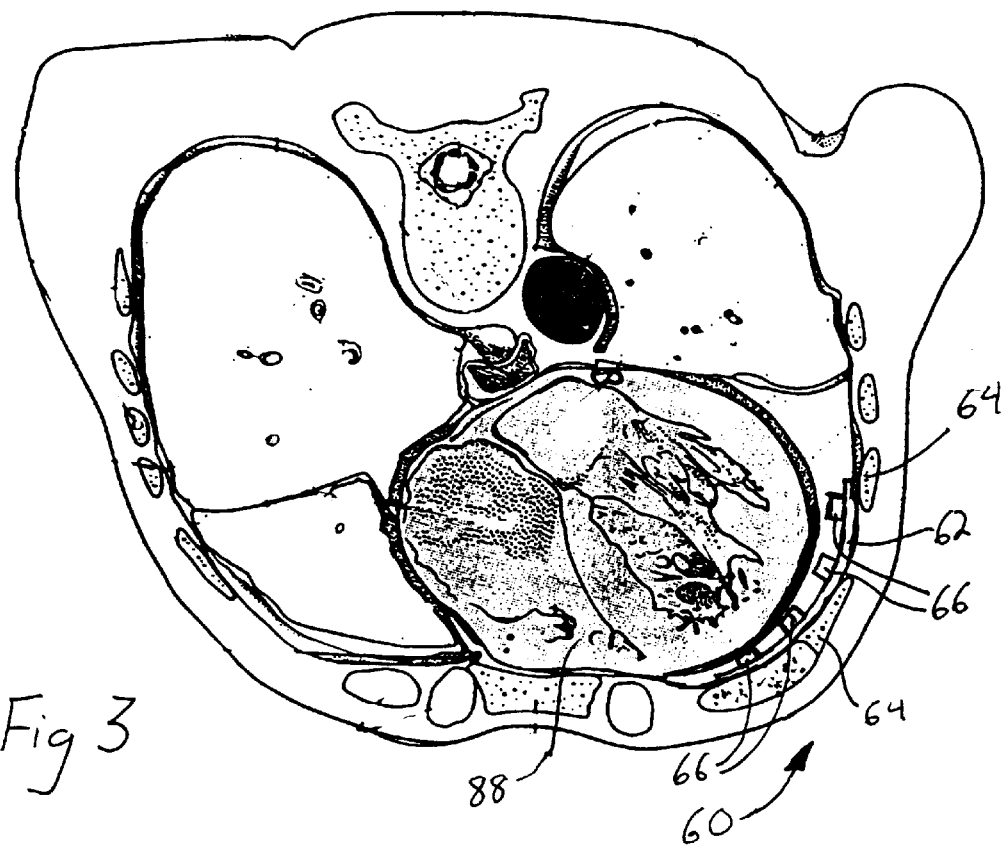
FIG. 3 is transverse cross sectional similar to that of FIG. 2 showing a second embodiment of the cardiac assist apparatus.

FIG. 3 illustrates another embodiment of an apparatus 60 which employs magnetic repulsive forces to assist a heart to contract. The second artificial contraction assist apparatus 60 has one or more brackets 62, similar to brackets 34 and 36, attached to the ribs 64 of the patient adjacent the heart's left ventricle. A plurality of voice coils 66 are mounted on the each bracket 62 and act as solenoids.

Figure 4:
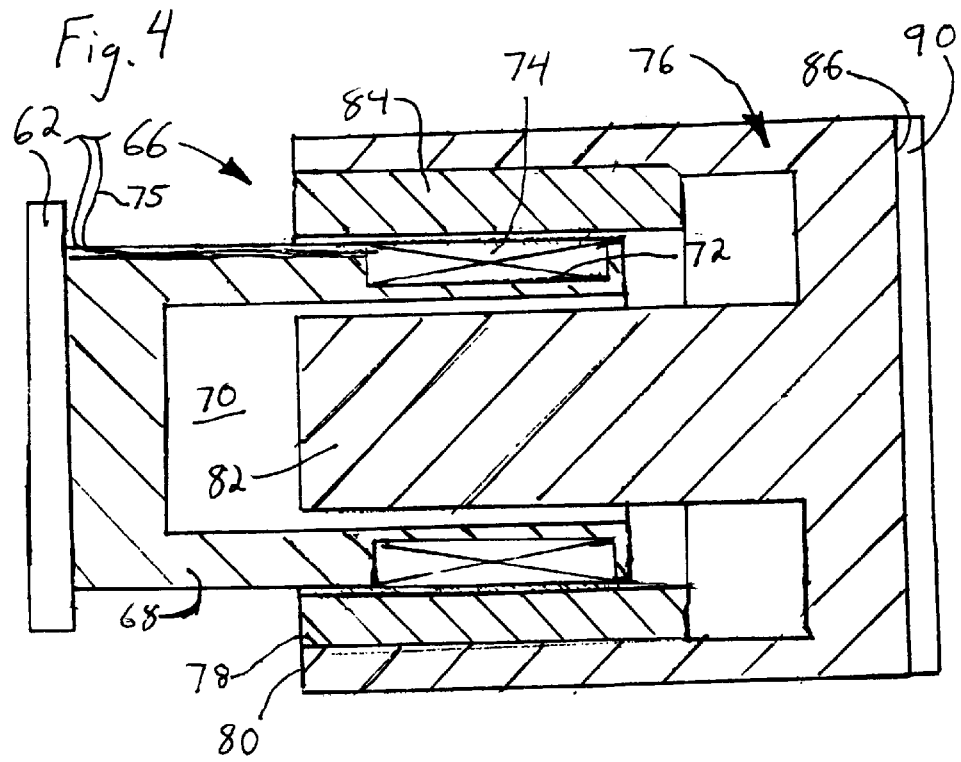
FIG. 4 illustrates a cross-section through a solenoid used in the second embodiment.

The voice coils 66 have identical construction with one of them shown in detail in FIG. 4. The voice coil 66 has a cylindrical coil holder 68 of magnetic material with a cavity 70 extending inwardly from one end. The outer circumferential surface of the coil holder 68 has a groove 72 adjacent the one end within which an electromagnetic coil 74 is wound. Wires 75 lead from the electromagnetic coil 74 to a controller similar to controller 46 in FIG. 1. A titanium armature 76 has an annular recess 78 extending inward from a first end 80 thereby forming a cylindrical center member 82. The center member 82 of the armature 76 is received within the cavity 70 of the coil holder 68. An annular permanent magnet 84 is press fit into the annular recess 78 of the armature and positioned around the electromagnetic coil 74 on the coil holder. When implanted into a patient, the remote end 86 of armature 76 rests against the surface of the heart 10.

In response to input signals from the sensors 48, the controller applies electrical pulses to the electromagnetic coil 74 of each voice coil 66. The resultant electromagnetic field interacts with the permanent magnet 84 to force the armature 76 away from the coil holder 68 and the bracket 62 attached to the ribs 64. This action pushes the remote end 86 of the armature against the surface of the heart 88 thereby compressing the left ventricle near the end of natural heart contraction. The surface area of the armature remote end 86 may be enlarged to spread the force over a wide region of the heart surface thereby reducing adverse affects due to the armature 76 repeatedly striking the same area of the heart. Such adverse affects may also be reduced by attaching pads to the surface of the heart, which pads are struck by the armature.

With continuing reference to FIG. 4, a hybrid of the two previously described apparatus utilizes a second electromagnet coil 90 attached to the remote end 86 of the armature 76. The second electromagnet coil 90 has a structure similar to that of coils 35 and 37 applied to the brackets in FIG. 1. In this hybrid embodiment, permanent magnets 28 and 30 also are attached to the surface of the heart adjacent each of the voice coils 66. In this version, current is applied to both of the electromagnet coils 74 and 90. As the armature 76 moves toward the heart, the magnetic field from the second electromagnet coil 90 repels the adjacent permanent magnet 28 or 30 producing contraction of the left ventricle. The movement of the armature may not actually contact the heart, instead the movement is used to maintain the second electromagnet coil 90 relatively close to the permanent magnet 28 or 30 as the heart contracts to maximize the magnetic repulsion and thus the contraction assist.

Further variations may include a telescoping armature which reduces the length of the voice coil in the retracted state between cardiac contractions, while increasing the effective distance of armature movement during a contraction. Also the voice coil 66 may be enclosed in a flexible membrane that is compatible with the heart tissue.

The foregoing description was primarily directed to a preferred embodiments of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

I claim:

1. An apparatus for artificially contracting a natural heart of an animal to pump blood, that apparatus comprising:

a member configured to be securely attached to a bone of the animal;

a first electromagnet coil mounted on the member and producing an electromagnetic field when an electric current is applied thereto; and a first permanent magnet configured to be disposed adjacent the first electromagnet coil, wherein the first permanent magnet produces a magnetic field which repulsively interacts with the electromagnetic field causing the first permanent magnet to apply a contracting force to the natural heart.

2. The apparatus as recited in claim 1 wherein the first permanent magnet is adapted to be attached to the natural heart.

3. The apparatus as recited in claim 1 further comprising a controller connected to the first electromagnet coil to selectively apply electrical current which results in the electromagnetic field being produced.

4. The apparatus recited in claim 3 further comprising a sensor connected to the controller for detecting cardiac activity of the animal.

5. The apparatus as recited in claim 1 wherein the first permanent magnet is attached to an armature with at least one of the armature and the first permanent magnet being received within the first electromagnet coil, and wherein application of electric current to the first electromagnet coil produces movement of the armature toward the natural heart.

6. The apparatus recited in claim 5 further comprising a second electromagnet coil coupled to the armature; and a second permanent magnet for attachment to the natural heart adjacent the second electromagnet coil.

7. The apparatus as recited in claim 1 wherein the member of first electromagnet coil comprises a bracket that is curved to conform to a rib of the animal.

8. An apparatus for artificially contracting a natural heart of an animal to pump blood, that apparatus comprising:
   a bracket configured to be securely attached to a bone of the animal;
   a plurality of electromagnet coils attached to the bracket with each electromagnet coil producing an electromagnetic field when an electric current is applied thereto; and
   a plurality of permanent magnets configured to be attached to the natural heart adjacent the plurality of electromagnet coils, wherein each permanent magnet produces a magnetic field which repulsively interacts with the electromagnetic field from an adjacent electromagnet coil causing each permanent magnet to apply a contracting force to the natural heart.

9. The apparatus as recited in claim 8 wherein the bracket is curved to conform to at least one rib of the animal.

10. The apparatus as recited in claim 8 further comprising a controller connected to the plurality of electromagnet coils to selectively apply electrical current which results in the electromagnetic field being produced.

11. The apparatus as recited in claim 10 further comprising a sensor connected to the controller for detecting cardiac activity of the animal.

12. An apparatus for artificially contracting a natural heart of an animal to pump blood, that apparatus comprising a plurality of solenoids configured to be attached to a bone of the animal adjacent the natural heart, each one of the plurality of solenoids comprises:
   a first electromagnet coil producing an electromagnetic field when an electric current is applied thereto;
   an armature movably mounted adjacent the first electromagnet coil; and
   a first permanent magnet attached to the armature, wherein the permanent magnet produces a magnetic field which interacts with the electromagnetic field to repel the armature away from the first electromagnet coil toward the natural heart.

13. The apparatus recited in claim 12 wherein each one of the plurality of solenoids further comprises a second electromagnet coil coupled to the armature; and a second permanent magnet adapted to be attached to the natural heart adjacent the second electromagnet coil.

14. The apparatus as recited in claim 12 further comprising a controller connected to the plurality of solenoids to selectively apply electrical current to each of the first electromagnet coils which results in the electromagnetic field being produced.

15. The apparatus as recited in claim 14 further comprising a sensor connected to the controller for detecting cardiac activity of the animal.

16. A method for artificially contracting a natural heart of an animal to pump blood, that method comprising steps of:
   securely attaching an electromagnetic coil to a bone of the animal, wherein the electromagnetic coil produces a first magnetic field when an electric current is applied thereto;
   positioning a permanent magnet adjacent to the electromagnetic coil, wherein the permanent magnet produces a second magnetic field; and
   selectively applying electric current to the electromagnetic coil to produce interaction of the first magnetic field with the second magnetic field which creates a repulsive force that causes contraction of the natural heart.

17. The apparatus as recited in claim 16 further comprising selectively applying electric current to the electromagnetic coil produce interaction of the first magnetic field with the second magnetic field which creates attraction force during cardiac diastole that causes expansion of the natural heart.

* * * * *